United States Patent
Porro et al.

(10) Patent No.: US 12,102,938 B2
(45) Date of Patent: Oct. 1, 2024

(54) DISTRIBUTION CHAMBER FOR LIQUID STREAM

(71) Applicant: Yara International ASA, Oslo (NO)

(72) Inventors: Lino Giovanni Porro, Etterbeek (BE); Luigi Serraiocco, Skien (NO)

(73) Assignee: Yara International ASA, Oslo (NO)

(*) Notice: Subject to any disclaimer, the term of this patent is extended or adjusted under 35 U.S.C. 154(b) by 188 days.

(21) Appl. No.: 17/797,410

(22) PCT Filed: Feb. 25, 2021

(86) PCT No.: PCT/EP2021/054662
§ 371 (c)(1),
(2) Date: Aug. 3, 2022

(87) PCT Pub. No.: WO2021/170709
PCT Pub. Date: Sep. 2, 2021

(65) Prior Publication Data
US 2023/0330557 A1    Oct. 19, 2023

(30) Foreign Application Priority Data
Feb. 25, 2020 (EP) ..................... 20159321

(51) Int. Cl.
*B01D 1/06* (2006.01)
*B01D 1/00* (2006.01)
(Continued)

(52) U.S. Cl.
CPC .............. *B01D 1/007* (2013.01); *B01D 1/06* (2013.01); *B01J 6/008* (2013.01); *C07C 273/02* (2013.01); *C07C 273/16* (2013.01)

(58) Field of Classification Search
CPC . B01D 1/007; B01D 1/06; B01J 6/008; C07C 273/02; C07C 273/16
See application file for complete search history.

(56) References Cited

U.S. PATENT DOCUMENTS 3,446,601 A * 5/1969 Heunks ................ C07C 273/04
564/71
3,495,952 A * 2/1970 Kadlec ...................... B01J 8/20
422/632

(Continued)

FOREIGN PATENT DOCUMENTS

| CN | 103657540 | 3/2014 |
| CN | 203899577 | 10/2014 |

(Continued)

OTHER PUBLICATIONS

International Search Report and Written Opinion issued in App. No. PCT/EP2021/054662, dated Jul. 19, 2021, 5 pages.

(Continued)

*Primary Examiner* — Jonathan Miller
(74) *Attorney, Agent, or Firm* — Dilworth IP, LLC (57) ABSTRACT

A distribution chamber suitable for distributing a liquid stream to a plurality of pipe openings distributed over a planar surface. The distribution chamber includes three perforated plates. A method to distribute a liquid stream to a plurality of pipe openings, a method to decompose ammonium carbamate from an aqueous solution comprising ammonium carbamate and a method to produce a concentrated aqueous urea solution from a diluted aqueous urea solution.

20 Claims, 2 Drawing Sheets

(51) Int. Cl.
  *B01J 6/00*    (2006.01)
  *C07C 273/02*  (2006.01)
  *C07C 273/16*  (2006.01)

(56) References Cited

U.S. PATENT DOCUMENTS

| | | | | |
|---|---|---|---|---|
| 3,498,755 | A * | 3/1970 | Borre | C10G 49/005 |
| | | | | 422/607 |
| 4,408,892 | A | 10/1983 | Combes | |
| 4,859,430 | A * | 8/1989 | Julian | B01J 8/44 |
| | | | | 34/585 |
| 5,407,647 | A * | 4/1995 | Tarancon | B01J 8/048 |
| | | | | 422/174 |
| 6,334,984 | B1 * | 1/2002 | Pagani | C07C 273/16 |
| | | | | 422/620 |
| 9,102,910 | B2 * | 8/2015 | Edwards | C12M 29/16 |
| 9,694,334 | B2 * | 7/2017 | Minola | B01J 10/002 |
| 11,186,542 | B2 * | 11/2021 | Scotto | B01J 19/244 |
| 2003/0172989 | A1 * | 9/2003 | Walter | B01J 8/0278 |
| | | | | 141/301 |
| 2004/0124124 | A1 * | 7/2004 | Pinho | B01J 8/0055 |
| | | | | 422/139 |
| 2006/0099118 | A1 * | 5/2006 | Filippi | F28F 3/04 |
| | | | | 422/198 |
| 2007/0272298 | A1 * | 11/2007 | Porscha | B01D 53/185 |
| | | | | 137/263 |
| 2011/0189054 | A1 | 8/2011 | Sheng | |
| 2011/0213186 | A1 * | 9/2011 | Di Girolamo | C07C 41/06 |
| | | | | 422/652 |
| 2016/0175795 | A1 * | 6/2016 | Minola | C07C 273/02 |
| | | | | 564/66 |
| 2017/0002466 | A1 * | 1/2017 | Delperier | F27B 5/16 |
| 2021/0187471 | A1 * | 6/2021 | Serraiocco | B01J 19/2425 |
| 2022/0008838 | A1 * | 1/2022 | Porro | B01D 1/0041 |
| 2022/0064109 | A1 * | 3/2022 | Porro | C07C 269/08 |
| 2023/0330557 | A1 * | 10/2023 | Porro | B01D 1/0064 |

FOREIGN PATENT DOCUMENTS

| | | |
|---|---|---|
| CN | 108946882 | 12/2018 |
| EP | 1195194 | 4/2002 |
| EP | 3244154 | 11/2017 |
| EP | 3513871 A1 | 7/2019 |
| WO | 0196288 | 12/2001 |

OTHER PUBLICATIONS

Yang, Shuai, "Structural optimistion of orifice uniformity of orifices for orifice-plate conical pulper", Journal of Nanjing Forestry University, vol. 40, No. 6, Nov. 15, 2016, 7 pages.

English translation of Chinese Office Action issued in App. No. CN202180016341, dated Aug. 9, 2023, 13 pages.

* cited by examiner

DISTRIBUTION CHAMBER FOR LIQUID STREAM

FIELD OF THE INVENTION

This invention relates to the field of urea synthesis, in particular it discloses a vertical distribution chamber suitable for distributing a liquid stream to a plurality of pipe openings distributed over a planar surface. The present invention also provides a method to distribute a liquid stream to a plurality of pipe openings, a method to decompose ammonium carbamate from an aqueous solution comprising ammonium carbamate and a method to produce a concentrated aqueous urea solution from a diluted aqueous urea solution.

BACKGROUND OF THE INVENTION

Urea is one of the most important chemicals industrially produced today, with around 200 million tons of urea being produced worldwide every year. Most of it (above 90% of total production) is used as a fertilizer in agriculture as a nitrogen source. Urea is produced by reacting ammonia ($NH_3$) and carbon dioxide ($CO_2$) in a two-step process: first, two molecules of ammonia react with one molecule of carbon dioxide to form ammonium carbamate ($H_2N-COONH_4$); secondly, ammonium carbamate decomposes into urea and water.

In order to manufacture urea on a large scale, a urea production plant comprises a plurality of equipment, such as reactors, concentrators, mixers, etc. . . . . In at least two stages during the manufacturing process, there is a need to divide a main liquid stream into a plurality of sub-streams and direct these sub-streams into pipes to be further heated up. Those two stages are in a carbamate decomposer and in a urea concentrator.

The dehydration of ammonium carbamate into urea mentioned above is not a quantitative process, i.e. a portion of the carbamate does not react, even when an excess of ammonia is introduced in the reactor to increase the yield of the carbamate formation. So, the stream coming out of the reactor is a liquid stream containing urea, ammonium carbamate, water and ammonia. To obtain a stream of urea with as little impurities as possible, the stream is directed into a decomposer, where the stream is divided into a plurality of streams that each enter a pipe in the main chamber of the decomposer. Each pipe is heated up with steam (or another heating medium, such as steam condensate or process vapors) so that the ammonium carbamate decomposes back to carbon dioxide and ammonia. Since carbon dioxide and ammonia are gases, they escape the liquid stream and can be recovered to be reinjected into the reactor and save raw material.

Such decomposition of ammonium carbamate in $NH_3$ and $CO_2$ gas can happen in different steps in series, working at different pressure, each decomposition step sending the recovered $NH_3$ and $CO_2$ to the Urea Reactor.

A vertical carbamate decomposer is often a cylindrical device comprising an injection chamber, or fluid distribution chamber, a heat exchanger, or stripper or decomposition section, comprising a plurality of parallel straight pipes and a collection chamber. The liquid stream comprising ammonium carbamate and urea is introduced in the injection chamber and separated in a plurality of sub-streams. Each sub-stream is directed to one of the straight pipes. The liquid stream flows to the collection chamber wherein the liquid phase essentially comprising urea and water is separated from the gaseous phase comprising carbon dioxide, ammonia and water vapor. The liquid streams and the gases are collected in their respective lines. The decomposer is usually built vertically, and the flow can be gravitational (top to bottom) or anti-gravitational (bottom to top). The pipes inside the decomposer are heated up, usually with steam, but other heating medium can be used, to induce the transformation of ammonium carbamate back into ammonia and carbon dioxide. A critical aspect for optimizing a decomposer operation is the injection profile of the stream into the pipes. The stream should enter the pipes in a homogeneous manner over the whole cross-section of the decomposer. If the flow is too high in some pipes and too low in others, the heat transfer will be affected: tubes with lower flow will have lower heat coefficient transfer than the others with the results that less heat will be given along these tubes and so less carbamate will be decomposed. The diameter of the inlet from which the aqueous solution comprising urea, water and ammonium carbamate is injected in the decomposer apparatus is usually much smaller than the diameter of the decomposition section, so a device is required to spread the flow of aqueous solution over the whole cross-section of the distribution chamber.

Once the stream of urea is cleaned from any impurities, it has usually a high amount of water, up to 30 weight %. To transform the stream into solid particles, there is a need to obtain a much more concentrated stream of urea. For example, if the stream is to be granulated in a prilling tower or a fluidized bed granulator, the liquid stream of urea should not contain more than 5 weight % of water. To achieve this goal, a urea concentrator may be used. To reach the desired water content, a single concentrator may be used, but it is also possible to use two or more concentrators set up one after the other to reduce the water content in stages. For example, a first concentrator may reduce the water content from 30 weight % to about 20 weight %. The stream produced by the first concentrator may be directed to a second concentrator where the water content is further reduced from 20 weight % to 5 weight %, or whatever water content is necessary for the solidification stage. A urea concentrator is built in a similar way as a carbamate decomposer: it comprises an injection or fluid distribution chamber, where the stream of the aqueous urea solution is introduced, a heat exchanger or evaporation section, comprising a plurality of parallel straight pipes where the liquid stream flows from the distribution chamber to a collection chamber. The pipes are heated up with steam (or other heating medium) and the water is evaporated as the stream flows in the pipes. In the collection chamber, the concentrated urea solution is separated from the water vapors and is directed to the granulation stage.

WO01/96288 (Urea Casale, 2001) describes a top-to-bottom carbamate decomposer comprising a plurality of horizontal perforated plates in the top section. The carbamate stream flows through these plates into the tube bundle. The perforated plates appear to lay directly perpendicular to the liquid stream and stretch from one side of the section to the other. The only example described comprises two perforated plates.

EP1195194 (Urea Casale, 2002) describes a carbamate decomposer comprising a distribution box which distributes the solution into the tube plate. The distribution box may be formed by a box of welded metal sheets. The box appears to lay perpendicular to the body of the decomposer, the orientation of the welded metal sheets is not mentioned.

There is a need to provide a new distribution chamber suitable for a urea concentrator or carbamate decomposer that can distribute a liquid stream evenly to a plurality of tubes. The distribution chamber should be as short as possible to limit the size of the complete device, and lead to a minimal pressure drop.

SUMMARY OF THE INVENTION

In its broadest aspect, this invention relates to a vertical distribution chamber for an apparatus comprising a first chamber and a second chamber, wherein the first chamber comprises a plurality of pipes for guiding a liquid stream from the distribution chamber to the second chamber and each pipe comprises a pipe opening fluidly connected to the distribution chamber, for evenly distributing a liquid stream to the plurality of pipe openings of the first chamber. The distribution chamber comprises: a) a body comprising an open circular end, a capped circular end, and a cylindrical wall along a central axis joining the open circular end and the capped circular end, wherein (i) the cylindrical wall has the same diameter as the open circular end and the capped circular end, and (ii) the open circular end is adapted to fit with the first chamber of the apparatus; (b) one inlet located on the capped circular end of the distribution chamber for feeding the liquid stream into the distribution chamber; and (c) a plurality of stacked plates comprising at least a first, a second, and a third perforated plate for distributing the flow of the liquid stream and directing the liquid stream into the plurality of pipes, wherein: (d) the first perforated plate has the shape of a cone, is centered on and perpendicular to the central axis of the distribution chamber, is located directly downstream of, particularly above, the inlet and the diameter of the base of the cone is about the size of the inlet of the distribution chamber; (e) the second perforated plate is a ring shaped disk-like plate centered on the central axis, and an outer diameter of about the diameter of the cylindrical wall and an inner diameter of about the diameter of the first perforated plate; (f) the third perforated plate is a disk that is positioned upstream of below the inlets of the plurality of pipes wherein substantially each perforation corresponds in size and location to the opening of a pipe from the plurality of pipes, and its diameter is about the same as the diameter of the open circular end of the distribution chamber.

More in particular, the present disclosure provides a vertical distribution chamber for an apparatus comprising a first chamber and a second chamber, wherein the first chamber comprises a plurality of pipes for guiding a liquid stream from the distribution chamber to the second chamber and each pipe comprises a pipe opening fluidly connected to the distribution chamber, for evenly distributing a liquid stream to the plurality of pipe openings, the distribution chamber comprising:

- a body comprising an open circular end, a capped circular end, and a cylindrical wall along a central axis joining the first open circular end and the second capped circular end, wherein:
  - the cylindrical wall has the same diameter as the open circular end and the capped circular end;
  - the open circular end is adapted to fit with the first chamber of the apparatus;
- one inlet located on the capped circular end of the distribution chamber for feeding the liquid stream into the distribution chamber, wherein the inlet is centered on the central axis of the distribution chamber;
- a series of stacked plates comprising at least a first, a second, and a third perforated plate, wherein:
- the first perforated plate has the shape of a cone pointing towards the open circular end, is centered on and perpendicular to the central axis of the distribution chamber, is located directly downstream of, particularly above, the inlet, the diameter of the base of the cone is 70% to 130% of the diameter of the inlet of the distribution chamber, and wherein the perforations make up from 1 to 10% of the surface of the first perforated plate;
- the second perforated plate is a ring-shaped disk-like plate centered on the central axis of the distribution chamber, has an outer diameter of about the diameter of the cylindrical wall and an inner diameter of about the diameter of the first perforated plate and wherein the perforations make up from 10 to 20% of the surface of the second perforated plate; and
- the third perforated plate is a disk, configured to be positioned from 5 mm to 25 mm upstream of, particularly directly below, the inlets of the plurality of pipes wherein each perforation in the third perforated plate is configured to align with a pipe opening in the first chamber and each pipe opening from the plurality of pipes of the first chamber has a corresponding perforation in the third perforated plate, each perforation is a circular through-hole and the diameter of each circular through-hole is 30% to 50% of the diameter of a pipe openings.

In another aspect, an apparatus, such as a carbamate decomposer or urea concentrator, comprising a distribution chamber according to the present disclosure, for distributing a liquid stream to a plurality of pipes in said apparatus is provided.

In another aspect, the use of a distribution chamber according to the present disclosure to distribute a liquid stream to a plurality of pipes is provided.

In another aspect, a method to distribute a liquid stream to a plurality of pipes, comprising the step of injecting the liquid stream into a distribution chamber according to the present disclosure is provided.

In another aspect, a method to decompose ammonium carbamate from a liquid stream comprising ammonium carbamate, comprising the steps of injecting the liquid stream comprising ammonium carbamate to a carbamate decomposer comprising a distribution chamber according to the present disclosure is provided.

In another aspect, a method to concentrate an aqueous solution, in particular an aqueous urea solution, comprising the step of feeding the aqueous solution to a concentrator comprising a distribution chamber according to the present invention is provided.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

All references cited in this description are hereby deemed to be incorporated in their entirety by way of reference.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, in particular+/−10% or less, more in particular+/−5% or less, even more in particular+/−1% or less, and even more in particular+/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints, for example "between A and B", includes all numbers and fractions subsumed within that range, as well as the recited endpoints.

The expression "weight percent", "% wt" or "weight %", here and throughout the description unless otherwise defined, refers to the relative weight of the respective component based on the overall weight of the formulation.

A truncated cone is a structure resulting from cutting a cone by a plane parallel to the base and removing the part containing the apex. It consists in two circular parallel ends with different diameters joined by a wall.

The ratio of the surface of the holes or perforations to the total surface of a plate or cone may be used to characterize the capacity of a plate to let the liquid through. The ratio surface of the holes divided by the surface of the cone may also be called the fraction of open area on the surface of the first plate or may be expressed as a percentage of the surface area of the perforated plate.

In its broadest aspect, this invention relates to a vertical distribution chamber for an apparatus comprising a first chamber and a second chamber, wherein the first chamber comprises a plurality of pipes for guiding a liquid stream from the distribution chamber to the second chamber and each pipe comprises a pipe opening fluidly connected to the distribution chamber, for evenly distributing a liquid stream to the plurality of pipe openings of the first chamber. The distribution chamber comprises: a) a body comprising an open circular end, a capped circular end, and a cylindrical wall along a central axis joining the open circular end and the capped circular end, wherein (i) the cylindrical wall has the same diameter as the open circular end and the capped circular end, and (ii) the open circular end is adapted to fit with the first chamber of the apparatus; (b) one inlet located on the capped circular end of the distribution chamber for feeding the liquid stream into the distribution chamber; and (c) a series or plurality of stacked plates comprising at least a first, a second, and a third perforated plate, for distributing the flow of the liquid stream and directing the liquid stream into the plurality of pipes, wherein: (d) the first perforated plate has the shape of a cone pointing towards the open circular end, is centered on and perpendicular to the central axis of the distribution chamber, is located directly downstream of, particularly above, the inlet and the diameter of the base of the cone is about the size of the inlet of the distribution chamber; (e) the second perforated plate is a ring-shaped disk-like plate centered on the central axis, with an outer diameter of about the diameter of the cylindrical wall, and an inner diameter of about the diameter of the first perforated plate; (f) the third perforated plate is a disk that is positioned upstream of the inlets of the plurality of pipes wherein substantially each perforation corresponds in size and location to the opening of a pipe from the plurality of pipes, and its diameter is about the same as the diameter of the open circular end of the distribution chamber.

The present invention also relates to an apparatus or reactor comprising a first chamber, a second chamber and a distribution chamber, wherein the first chamber comprises a plurality of pipes for guiding a liquid stream from the distribution chamber to the second chamber and each pipe comprises a pipe opening fluidly connected to the distribution chamber; wherein the second chamber is a collection chamber; and wherein the distribution chamber is a distribution chamber for evenly distributing a liquid stream to the plurality of pipe openings of the first chamber according to the present application. In particular embodiments, the apparatus comprising a first chamber and a second chamber as envisaged herein is configured to operate with a bottom-to-top liquid flow, wherein the third perforated disk in the distribution chamber is positioned below the inlets of the plurality of pipes.

It was found that a combination of three different perforated plates enabled an even distribution of the liquid stream over the whole circular open end of the distribution chamber. The first two plates encountered by the liquid stream distributes the stream over the whole cross-section of the distribution chamber and the third plate, which is aligned with the plurality of pipes of the first chamber, ensures that the stream of liquid is centered on and aligned with each pipe.

To obtain a satisfying heat transfer in as many pipes as possible in the first chamber of the apparatus, it is important that the stream entering each pipe is as symmetrical as possible around the axis of the pipe and that the flow or velocity of the streams in each pipe is as homogeneous as possible over the whole cross section of the distribution chamber.

The capped end may be capped with different designs, such as a hemispherical structure or a conical shape.

In one embodiment, the inlet is centered on the central axis of the distribution chamber. This may be desirable in order to obtain an evenly distributed flow over the cross-section of the distribution chamber.

In one embodiment, the diameter of the inlet is from 5% to 35%, from 5% to 30%, from 10% to 35%, from 10% to 30%, from 5% to 25%, or from 10% to 25% of the diameter of the cylindrical wall of the distribution chamber.

In one embodiment wherein the diameter of the cylindrical wall of the distribution chamber is from 80 to 200 cm, the diameter of the inlet may be from 2 to 30 cm, from 2 to 25 cm, from 2 to 20, from 5 to 30 cm, from 5 to 25 cm, from 5 to 20 cm, or from 8 to 30 cm.

Since the distribution chamber has an open circular end and a cylindrical body, it may be an advantage that all the perforated plates have a central symmetry centered on the central axis of the distribution chamber.

In one embodiment, the cylindrical body of the distribution chamber has a diameter of from 20 to 250 cm, from 30 to 250 cm, from 40 to 250 cm, from 20 to 200 cm, from 20 to 180 cm, from 30 to 200 cm, from 30 to 180 cm, from 40 to 200 cm, or from 40 to 180 cm.

It may be preferable to limit the height of the distribution chamber as much as possible to reduce the size of the carbamate decomposer.

First Perforated Plate

The first perforated plate has the shape of a cone pointing towards the open circular end, and is centered on and perpendicular to the central axis of the distribution chamber. It is located directly downstream of, particularly above, the inlet and the diameter of the base of the cone is about the size of the inlet of the distribution chamber.

The first plate is the plate closest to the inlet of the distribution chamber and the first obstacle that the liquid stream meets after it has entered the distribution chamber.

The first plate has the role of directing a first portion of the stream towards the pipes located in the center of the first section of the apparatus and diverting the remainder of the liquid stream towards the sides of the distribution chamber, and a conical design with holes, i.e. a perforated cone, and a diameter of about the same size as the inlet of the distribution chamber was found to achieve the desired effect. A smaller diameter would not distribute the liquid on an area large enough. A larger diameter would not achieve a better result because of the flow profile of the liquid stream. The portion of the liquid stream passing through the first plate may be adjusted by modifying the size of the holes or perforations of the first plate. The larger the holes the greater the flow passing through. The holes may be evenly distributed over the cone to ensure an even distribution of the liquid stream above the perforated plate.

The ratio of the surface of the holes or perforations to the total surface of a plate or cone may be used to characterize the capacity of a plate, particularly the first plate, to let the liquid through. The ratio surface of the holes divided by the surface of the cone may also be called the fraction of open area on the surface of the first plate or may be expressed as a percentage of the surface area of the perforated plate.

In one embodiment, the ratio surface of the holes divided by the surface of the cone for the first plate is from 0.01 to 0.1, from 0.01 to 0.09, from 0.02 to 0.1, from 0.03 to 0.1, from 0.02 to 0.09, from 0.03 to 0.09, or from 0.02 to 0.08. Stated differently, the perforations of the first plate make up from 1 to 10%, from 1 to 9%, from 2 to 10%, from 3 to 10%, from 2 to 9%, from 3 to 9% or from 2 to 8% of the surface of the first perforated plate.

In one embodiment, the holes of the first perforated plate are circular holes or perforations with a diameter from 1.0 to 7.0 mm, from 1.5 to 5.0 mm, from 2.0 to 5.0 mm, or from 2.5 to 4.5 mm. In one embodiment, the holes of the first perforated plate have a diameter of 1.5, 2.0, 2.5, 3.0, 3.5, 4.0, 4.5, 5.0, or 5.5 mm.

In one embodiment, the holes or perforations on the first perforated plate form a plurality of staggered rows.

In one embodiment, the holes on the first perforated plate are separated from each other by a distance comprised from 15 to 45 mm, from 15 to 30 mm, from 20 to 35 mm, from 20 to 40 mm, or from 15 to 40 mm. In one embodiment, the holes on the first perforated plate are separated from each other by 10, 15, 20, 25, 30, 35, 40, or 45 mm.

The first perforated plate also allows to spread the liquid stream across a larger area than the inlet. The first plate is designed so that only a portion of the liquid stream injected in the distribution chamber goes through its perforations. The other portion of the liquid stream has to flow outside its edges and therefore already increases its distribution.

In one embodiment, the diameter of the first perforated plate is comprised from 70% to 130%, from 70% to 120%, from 70% to 110%, from 80% to 130%, from 80% to 120%, from 80% to 110%, from 90% to 130%, from 90% to 120, or from 90% to 110% of the diameter of the inlet for a liquid stream of the distribution chamber. In one embodiment, the diameter of the first perforated plate is equal to the diameter of the inlet of the distribution chamber plus or minus 10%. In one embodiment, the diameter of the first perforated plate is equal to the diameter of the inlet of the distribution chamber plus or minus 5%.

In one embodiment, the first perforated plate is a right circular cone. A right circular cone is a cone with a circular base and the axis passing by the top of the cone and at a right angle to the base passes through the center of the base.

In one embodiment, the first perforated plate is a right circular cone with an opening angle comprised from 40° to 80°, from 45° to 75°, or from 50° to 70°, wherein the opening angle of a cone is defined by the angle between the cone axis and the cone surface. In one embodiment, the first perforated plate is a right circular cone with an opening angle of 60°.

In one embodiment, the first perforated plate is located 5.0 to 20 cm, 5.0 to 15 cm, 7.0 to 15 cm, 7.0 to 20 cm, or 8.0 to 12 cm, above the inlet of the distribution chamber. The exact position of the first perforated plate may be adjusted depending on the other parameters of the distribution chamber.

Second Plate

Since the difference between the diameter of the liquid inlet and the diameter of the first chamber of the apparatus, in particular the decomposition section, is so large, the first plate is not sufficient to distribute the solution over the whole cross-section of the distribution chamber. A second plate with a larger diameter was found necessary to enable proper distribution of the liquid stream to the tubes or pipes located on the periphery of the cross section. The second perforated plate should be ring-shaped or hollow in the middle to not disturb the distribution profile of the stream created by the first perforated plate. The second perforated plate should have an outer diameter, which is about the same as the diameter of the cylindrical wall to distribute the liquid stream over the entire cross-section of the distribution chamber, particularly the open end of the distribution chamber. In one embodiment, the second perforated plate is a simple ring-shaped disk with an outer diameter that is about the same as the diameter of the cylindrical wall and an inner diameter that is about the size of the first perforated plate.

In one embodiment, the second perforated plate has a circular symmetry, i.e. the second perforated plate comprises an axial symmetry.

In one embodiment, the ratio surface of the holes divided by the surface of the second plate is from 0.10 to 0.20, from 0.10 to 0.19, from 0.10 to 0.18, from 0.11 to 0.20, from 0.11 to 0.19, from 0.11 to 0.18, from 0.12 to 0.20, from 0.12 to 0.19 or from 0.12 to 0.18. Stated differently, the perforations make up from 10 to 20%, from 10 to 19%, from 10 to 18%, from 11 to 20%, from 11 to 19%, from 11 to 18%, from 12 to 20%, from 12 to 19%, or from 12 to 18% of the surface of the second perforated plate.

In one embodiment, the holes of the second perforated plate have a diameter of from 4.0 to 10.0 mm, from 4.5 to 10.0 mm, from 4.5 to 9.0 mm, from 5.0 to 9.0 mm, from 5.0 to 8.5 mm, or from 5.0 to 10.0 mm. In one embodiment, the holes of the second perforated plate have a diameter of 4.0, 4.5, 5.0, 5.5, 6.0, 6.5, 7.0, 7.5, 8.0, 8.5, 9.0, 9.5, or 10.0 mm.

In one embodiment, the holes on the second perforated plate form a plurality of staggered rows.

In one embodiment, the holes on the second perforated plate are separated from each other by a distance of from 15 to 45 mm, from 15 to 30 mm, from 20 to 35 mm, from 20 to 40 mm, or from 15 to 40 mm. In one embodiment, the holes on the first perforated plate are separated from each other by 10, 15, 20, 25, 30, 35, 40, or 45 mm.

The exact diameter of the holes, their position and distance to each other may be adjusted based on simple simulations to optimize the design of each distribution chamber based on other characteristics of the distribution chamber, such as intended use, or characteristics of the fluid to be dispersed.

In one embodiment, the second perforated plate comprises a non-perforated section, in particular the outer section of the second perforated plate is not perforated. In particular, the non-perforated section thus forms a ring-shaped section on the second perforated plate, with an outer diameter equal to the outer diameter of the second perforated plate, and an inner diameter of 90% to 99% of the outer diameter of the second perforated plate.

In one embodiment, the area of the non-perforated section represents 1 to 10% of the area of the second perforated plate.

In one embodiment, the second perforated plate is located 1.0 to 10 cm, 1.0 to 8.0 cm, 1.0 to 6.0 cm, 1.0 to 5.0, 0.5 to 10 cm, 0.5 to 8.0 cm, 0.5 to 6.0 cm, or 0.5 to 5.0 cm downstream of, particularly above the first perforated plate. It has been observed that the location of the second perforated plate has not much impact on the performance of the device.

In one embodiment, the second perforated plate has a semi-toroidal shape. A semi-toroidal shape is a three-dimensional disk-like structure, wherein its projection on a horizontal cross-section of the distribution chamber is ring shaped or in the shape of a hollow disk. Examples of semi-toroidal shape are given in FIG. 1. The semi-toroidal shape may comprise a single rounded shape, such as represented in FIG. 2a or it may also comprise several elements assembled together, such as represented in FIG. 2b. The FIG. 2b only represents one half of the plate to facilitate the understanding of the design. It was found that the simple design of a two-dimensional hollow disk could be modified to a three-dimensional structure to further improve the distribution of the liquid stream.

In one embodiment, the second plate has a semi-toroidal shape and consists of three different sections. Each section is a truncated cone and they are joined together in the following manner: the section with the largest diameter, referred to as first section or first cone, is not perforated. It is pointing towards the open circular end of the distribution chamber at a first angle, and restricts the flow around its edge. The top of its cone, i.e. the circle with the smallest of the two diameters, is joined to the base of the second truncated cone, or second section. The second truncated cone is also pointing towards the circular end of the distribution chamber, although at a different second angle than the first truncated cone. The second truncated cone is perforated with holes to let the liquid or aqueous solution flow through. These holes may be evenly distributed over the second truncated cone. The top of the second truncated cone is joined with the base of the third truncated cone. The third truncated cone is pointing in the other direction of the two previous sections, i.e. pointing towards the capped circular end of the distribution chamber. The third truncated cone is perforated to let the liquid or aqueous solution flow through. An embodiment of such a perforated plate is provided in FIG. 2b (only half of the plate is drawn to improve understanding of the design). In one embodiment, the holes on the third truncated cone are evenly distributed. After passing the second plate, the aqueous solution is distributed on a larger portion of the cross-section of the distribution chamber. The combination of the three sections gives a semi-toroidal shape to the second plate instead of a flat disk.

In one embodiment, the second plate has a semi-toroidal shape as explained above, wherein the wall of the first truncated cone which is not perforated forms an angle of 45 to 85°, 45 to 80°, 45 to 70°, 50 to 85°, 50 to 80°, 50 to 70°, or 60 to 70°, with its base.

In one embodiment, the second plate has a semi-toroidal shape as explained above, wherein the non-perforated wall of the first truncated cone has a length of from 1% to 10%, or from 1% to 8%, or from 1% to 5% of the diameter of the cylindrical wall of the distribution chamber.

In one embodiment, the second plate has a semi-toroidal shape as explained above, wherein the wall of the first truncated cone has a length of from 10 to 50 mm.

In one embodiment, the second plate has a semi-toroidal shape as explained above, wherein the wall of the second truncated cone forms an angle of 10° to 30°, 10° to 25°, 15° to 30°, 15° to 25°, or 10° to 20° with its base.

In one embodiment, the second plate has a semi-toroidal shape as explained above, wherein the wall of the second truncated cone has a length of from 10 to 25 cm, from 15 to 25 cm, or from 10 to 20 cm.

In one embodiment, the second plate has a semi-toroidal shape as explained above, wherein the wall of the second truncated cone has a length of 11, 12, 13, 14, 15, 16, 17, 18, 19, 20, 21, 22, 23, 24, or 25 cm.

In one embodiment, the second plate has a semi-toroidal shape as explained above, wherein the wall of the second truncated cone has a length of from 15% to 40%, from 20% to 40%, from 20 to 35%, or from 15% to 35% of the diameter of the cylindrical wall of the distribution chamber.

In one embodiment, the second plate has a semi-toroidal shape as explained above, wherein the wall of the second c truncated one has a length of about 15 cm or 25% of the diameter of the cylindrical wall of the distribution chamber.

In one embodiment, the second plate has a semi-toroidal shape as explained above, and the ratio surface of the holes divided by the surface of the cone of the second cone is from 0.10 to 0.20, from 0.10 to 0.19, from 0.10 to 0.18, from 0.11 to 0.20, from 0.11 to 0.19, from 0.11 to 0.18, from 0.12 to 0.20, from 0.12 to 0.19 or from 0.12 to 0.18. Stated differently, the perforations make up from 10 to 20%, from 10 to 19%, from 10 to 18%, from 11 to 20%, from 11 to 19%, from 11 to 18%, from 12 to 20%, from 12 to 19%, or from 12 to 18% of the surface area of the second truncated cone.

In one embodiment, the second plate has a semi-toroidal shape as explained above, wherein the wall of the third truncated cone forms an angle of 30° to 60°, 30° to 55°, 30° to 50°, 35° to 60°, 35° to 55°, or 35° to 50° with its base.

In one embodiment, the second plate has a semi-toroidal shape as explained above, wherein the wall of the third truncated cone has a length of from 2.0 to 7.0 cm, from 2.5 to 7.0 cm, from 3.0 to 7.0 cm, from 2.0 to 6.5 cm, from 2.5 to 6.5 cm, from 3.0 to 6.5 cm, or from 3.0 to 6.0 cm.

In one embodiment, the second plate has a semi-toroidal shape as explained above, and the ratio surface of the holes divided by the surface of the cone of the third truncated cone is from 0.10 to 0.20, from 0.10 to 0.19, from 0.10 to 0.18, from 0.11 to 0.20, from 0.11 to 0.19, from 0.11 to 0.18, from 0.12 to 0.20, from 0.12 to 0.19 or from 0.12 to 0.18. Stated differently, the perforations make up from 10 to 20%, from 10 to 19%, from 10 to 18%, from 11 to 20%, from 11 to 19%, from 11 to 18%, from 12 to 20%, from 12 to 19%, or from 12 to 18% of the surface area of the third truncated cone.

The second perforated plate may be an essentially flat object, such as a disk with a certain thickness, but it may also be a three-dimensional disk-like structure, such as the semi-toroidal shape explained above. Where the second perforated plate is a three-dimensional disk-like structure, the height of the second perforated plate may be at least 1.0, 2.0, 3.0, 4.0, 5.0, 7.0, 8.0 cm. Where the second perforated plate is a semi-toroidal structure as disclosed above, the height of the plate depends on the length of the first two portions or truncated cones and the angle of each wall related to its base.

In one embodiment, the diameter of the base of the first truncated cone of the second perforated plate is substantially the same as the diameter of the wall. It may be desirable that the diameter of the base of the first cone is about the same as the diameter of the wall. This improves the flow profile above the second plate.

In one embodiment, the diameter of the base of the first truncated cone of the second perforated plate is 1 to 10 mm smaller than the diameter of the wall. It may be desirable to leave a gap between the wall of the distribution chamber and the base of the first truncated cone of the second plate to avoid material build-up in the corner between the cone and the wall of the chamber. A material build-up could lead to corrosion and damage the distribution chamber.

In one embodiment, the second perforated plate is located from 1.0 to 10 cm, from 1.0 to 8.0 cm, from 1.0 to 6.0 cm, from 1.0 to 5.0, from 0.5 to 10 cm, from 0.5 to 8.0 cm, from 0.5 to 6.0 cm, or from 0.5 to 5.0 cm above the first perforated plate. It has been observed that the location of the second perforated plate has not much impact on the performance of the device.

In one embodiment, where the second plate has a semi-toroidal shape as explained above, the base of the first truncated cone may be located from 0.1 to 2.0 cm, from 0.1 to 1.5 cm, or from 0.1 to 1.0 cm above the base of the first perforated plate.

Third Perforated Plate

The third perforated plate is a flat disk that is positioned in front of the inlets of the plurality of pipes of the first chamber of the apparatus, wherein the location of each perforation is directly upstream of, particularly directly below, the opening of a pipe from the plurality of pipes of the first chamber of the apparatus, and the diameter of the third perforated plate is about the same as the diameter of the open circular end of the distribution chamber. Its role is to ensure that the liquid enters the pipes in a centered and quasi-symmetrical manner to obtain the best effect in the first chamber of the apparatus. Each perforation in the plate matches and is aligned with a pipe in the first chamber and each pipe from the plurality of pipes of the first chamber has a corresponding perforation in the third perforated plate. The plate should cover all the pipes of the decomposition section, so its diameter should be about the same as the circular end of the distribution chamber. The size of the perforations in the third perforated plate should be smaller than the diameter of a pipe from the plurality of pipes.

In one embodiment, the perforations of the third plate are circular holes, wherein the diameter of each circular hole is 30% to 50% of the diameter of the pipe openings of the first chamber.

In one embodiment, the diameter of the third perforated plate is 1 to 10 mm smaller than the diameter of the wall. It may be desirable that the diameter of the fourth plate is a bit smaller than the chamber itself to avoid a build-up of corrosive material in the corner between the plate and the wall of the chamber. A gap of a few millimeters was found to be enough to avoid this undesirable effect. However, a large gap is not desirable as this will affect the distribution of the liquid in the pipes.

In one embodiment, the third perforated plate is located from about 5 mm to about 25 mm upstream of, particularly below the inlets of the plurality of pipes, in particular from 7 to 15 mm, in particular about 10 mm below the inlets. If the third plate is too close or too far to the inlets, the flow profile of the liquid entering the pipes may not be satisfactory, for example, it may not be centered in the pipes, which lead to a poorer performance of the decomposition section, i.e. not all the ammonium carbamate is decomposed when the liquid reaches the collection chamber. Moreover, if the third plate is too close, virtually attached to the inlets, stagnant area can result between the inlets, leading to build up of corrosive material. If the plate is too far from the inlets, the flow will be too dispersed and again the performance of the decomposition section will be reduced. It was found that a distance of between 5 and 25 mm between the third perforated plate and the pipe openings was suitable to obtain satisfactory results. In one embodiment, the distance is about 10 mm.

The distance between the third plate and the pipe openings may be dependent on the ratio of the diameter of the perforations of the third plate and the diameter of the pipe openings of the first chamber. The larger the perforations are, the closer the third plate should be to the pipe openings. In one embodiment, the perforations of the third perforated plate are circular with a diameter of 5 to 9 mm, in particular 6 to 8 mm. The plurality of pipes used in chemical engineering equipment have a typical diameter of 15 to 25 mm, in particular of 15 to 20 mm. As mentioned above, it may be an advantage that the perforations are smaller than the pipes to obtain a better flow profile in the pipes.

In one embodiment, the thickness of the third plate is from 3 to 15 mm, from 3 to 10 mm, or from 3 to 8 mm. The third plate should be thick enough to withstand the pressure of the liquid stream.

Fourth Perforated Plate (Optional)

In one embodiment, the decomposition chamber comprises a fourth perforated plate.

The fourth perforated plate is a perforated flat disk. The fourth perforated plate is located between the second and the third perforated plates and is a perforated disk. It is centered on the central axis of the chamber and also perpendicular to it. It is located directly above the inlet and its diameter is about the size of the inlet of the distribution chamber. Its role is to regulate further the liquid flow in the central portion of the chamber and to divert a portion of the flow radially towards the sides of the distribution chamber. For example, the fourth perforated plate may be used to reduce the dynamic pressure of the solution in the center part of the distribution chamber.

In one embodiment, the diameter of the fourth perforated plate is from 70 to 130%, from 70 to 120%, from 70 to 110%, from 80 to 130%, from 80 to 120%, from 80 to 110%, from 90 to 130%, from 90 to 120, or from 90 to 110% of the diameter of the inlet for a liquid stream of the distribution chamber.

In one embodiment, the diameter of the fourth perforated plate is from 8.0 to 20 cm, from 8.0 to 18 cm, from 9.0 to 18 cm, from 9.0 to 16 cm, from 10 to 20 cm, from 10 to 18 cm, from 10 to 16 cm, or from 8.0 to 16 cm. In one embodiment, the diameter of the fourth perforated plate is from 10 to 40%, from 15 to 40%, from 10 to 35%, from 15 to 35%, from 15 to 30%, or from 15 to 25% of the diameter of the cylindrical wall of the distribution chamber.

In one embodiment, the ratio surface of the holes divided by the surface of the cone of the fourth plate is from 0.03 to 0.1, from 0.03 to 0.09, from 0.04 to 0.1, from 0.05 to 0.1, from 0.04 to 0.09, from 0.05 to 0.09, or from 0.04 to 0.08. Stated differently, the perforations make up from 3 to 10%, from 3 to 9%, from 4 to 10%, from 5 to 10%, from 4 to 9%, from 5 to 9%, or from 4 to 8% of the surface are of the fourth plate.

In one embodiment, the holes of the fourth perforated plate have a diameter of from 4.0 to 15 mm, from 5.0 to 15 mm, from 5.0 to 14 mm, from 5.0 to 13 mm, from 5.0 to 12 mm, or from 6.0 to 15 mm. In one embodiment, the holes of the second perforated plate have a diameter of 4.0, 4.5, 5.0, 5.5, 6.0, 6.5, 7.0, 7.5, 8.0, 8.5, 9.0, 9.5, 10.0, 11, 12, 13, 14 or 15 mm.

In one embodiment, the holes on the fourth perforated plate form a plurality of staggered rows.

In one embodiment, the holes on the second perforated plate are separated from each other by a distance comprised from 20 to 60 mm, from 25 to 60 mm, from 30 to 60 mm, from 20 to 55 mm, from 25 to 55 mm, from 30 to 55 mm, from 20 to 50 mm, from 25 to 50 mm, or from 30 to 50 mm. In one embodiment, the holes on the first perforated plate are separated from each other by 10, 15, 20, 25, 30, 35, 40, 45, 50, 55, or 60 mm.

In one embodiment, the fourth perforated plate may be located 0.1 to 10.0 cm, 0.1 to 5.0 cm, or 0.1 to 2.5 cm, above the highest point of the second perforated plate.

In one embodiment, the diameter of the distribution chamber is from 0.35 m to 3 m. The size of the distribution chamber needs to be adapted to the specific requirements of each apparatus to which the distribution chamber is fluidly connected to. A typical size of such a chamber may be comprised between 0.35 and 3 m.

The distribution chamber and the perforated plates are made in a material that is suitable for the operating conditions. Among other things, it should be resistant to corrosion. Suitable materials are well known in the field of chemical engineering.

In another aspect, the use of a distribution chamber according to the present disclosure to distribute a liquid stream to a plurality of pipes is provided.

Method

In another aspect, a method to distribute a liquid stream to a plurality of pipes, comprising the step of feeding the liquid stream into a distribution chamber according to the present disclosure is provided and providing a heating fluid to the pipes of the carbamate decomposer, wherein the liquid stream has a velocity of from 0.2 to 2.0 m/s.

The liquid stream fed into the distribution chamber may comprise one or more of urea, ammonium carbamate, ammonium carbonate, ammonium bicarbonate or ammonia. The liquid stream has a velocity of from 0.2 to 2.0 m/s. A lower velocity causes the liquid stream to stagnate in the distribution chamber. A velocity above 2.0 m/s may damage the device, in particular the nozzle injecting the liquid stream into the distribution chamber.

When a liquid stream, in particular an aqueous solution, is directed in the inlet of the distribution chamber, it goes through three, optionally four, perforated plates to achieve an essentially even distribution in a cross-section of the distribution chamber and the last perforated plate located upstream of, particularly below, the opening of the plurality of pipes ensures that the flow leaving the distribution chamber is centered on each pipe opening.

In another aspect, a method to decompose ammonium carbamate from a liquid stream comprising ammonium carbamate is provided, the method comprising the steps of feeding a liquid stream comprising ammonium carbamate to a carbamate decomposer comprising a distribution chamber according to the present disclosure and providing a heating fluid to the pipes of the carbamate decomposer wherein the liquid stream comprising ammonium carbamate has a velocity of from 0.2 to 2.0 m/s.

In another aspect, a method to concentrate a urea solution is provided, the method comprising the steps of feeding a liquid stream comprising urea to a concentrator comprising a distribution chamber according to the present disclosure is provided and providing a heating fluid to the pipes of concentrator wherein the liquid stream comprising urea has a velocity of from 0.2 to 2.0 m/s.

Figure 1:
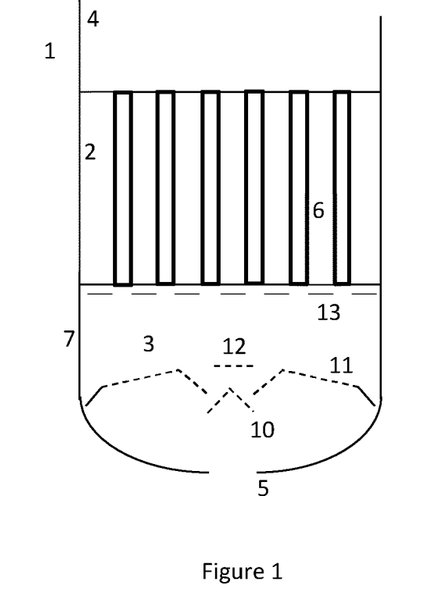
FIG. 1 describes a carbamate decomposer apparatus comprising a first chamber, which is a heat exchange or decomposition section, a second chamber, which is a collection chamber, and an embodiment of a distribution chamber according to the present disclosure.
Figure 2A:
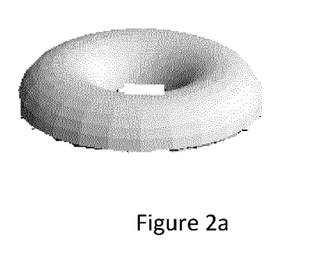
FIGS. 2a-2b represent two of the possible structural profiles of the second perforated plate of a distribution chamber according to the present disclosure.
Figure 2B:
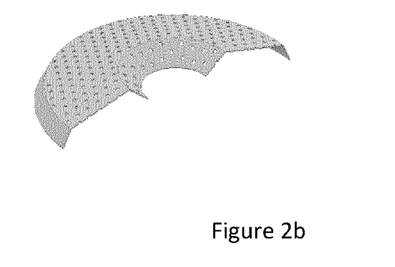

FIG. 1 describes a carbamate decomposer apparatus 1 comprising a first chamber 2, which is a decomposition section, a second chamber 4, which is a collection chamber, and an embodiment of a distribution chamber 3 according to the present disclosure. The decomposition section comprises a plurality of pipes 6 to guide the liquid stream comprising ammonium carbamate from the distribution chamber to the collection chamber. The distribution chamber comprises a circular end adapted to fit with the decomposition section, a cylindrical wall 7 and a second end capped with a hemisphere and comprising an inlet 5 for feeding the liquid stream comprising ammonium carbamate. A perforated cone 10, where its base diameter is about the same as the inlet, is located directly above the inlet, about 10 to 15 cm above the inlet, and is centered on and perpendicular to the main axis of the distribution chamber. The cone 10 has a ratio surface of perforations to surface of the cone of about 3% to 4%. The perforations are preferably circular through-holes since these are easier to manufacture. The diameter and number of the holes may be modified as long as the ratio surface of holes to surface of the cone 10 is kept within the desired range. A second perforated plate 11 is located above the first cone 10. The second plate comprises three sections, each section being a truncated cone, joined together. The truncated cone with the largest diameter is not perforated. The second largest truncated cone is pointing upwards, towards the open circular end of the distribution chamber 3, and the third truncated cone is pointing downwards, towards the inlet 5. The second plate forms a semi-toroidal like structure with a hollow space in its center, the hollow space being a disk with a diameter 1 to 20% larger than the perforated cone 10. The base of the first truncated cone with the largest diameter is located 1 to 10 cm above the base of the perforated cone 10. The largest diameter of the second plate is 2 mm smaller than the diameter of the wall of the chamber. The second and third truncated cones of the plate 11 has a ratio surface of perforations to surface of the cone of about 13% to 15%. The perforations are preferably circular through-holes since these are easier to manufacture. The perforations are evenly distributed on the surface of the second and third truncated cones. The fourth perforated plate 12 is located above the second plate 11, in particular from 1 to 10 cm above the second plate 11, and has about the same diameter as the inlet 5. The cone 12 has a ratio surface of perforations to surface of the cone of about 5 to 8%, and the perforations are evenly distributed across its surface. The third perforated plate 13 is located above the fourth plate and 10 mm below the inlets of the pipes 6. Its diameter is 2 mm smaller than the diameter of the wall of the chamber. The holes on the plate match with the inlets of the pipes 6 and have a diameter 40 to 50% smaller than the pipe openings. The four perforated plates are centered on and perpendicular to the main axis of the distribution chamber. Flow simulations of the decomposition chamber using a liquid stream with a velocity of 1.5 m/s showed a satisfying standard deviation (0.00464) of the vertical velocity in the tubes. Flow simulations on a distribution chamber comprising the first plate 10, the second plate 11 and the third plate 13, showed a higher standard deviation (0.02617) of the vertical velocity in the tubes than the case above, but is still deemed acceptable.

Figure 3:
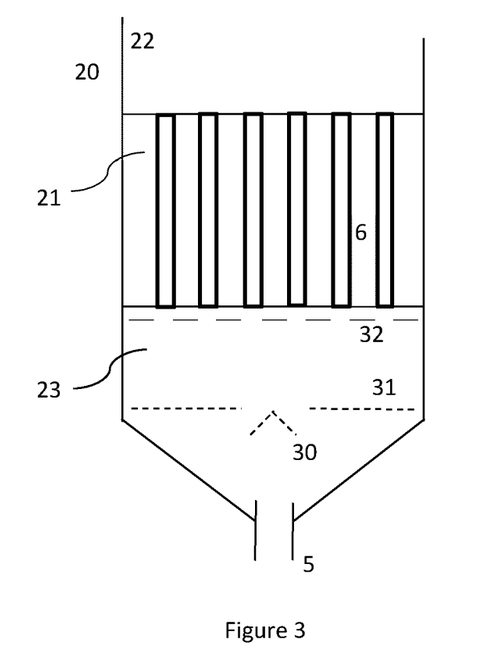
FIG. 3 describes a urea concentrator comprising a first chamber, which is a heat exchange or evaporation section, a second chamber, which is a collection chamber, and an embodiment of a distribution chamber according to the present disclosure.

FIG. 3 describes a urea concentrator 20 comprising a first chamber 21, which is a heat exchange or evaporation section, a second chamber 22, which is a collection chamber, and an embodiment of a distribution chamber 23 according to the present disclosure. The heat exchange or evaporation section comprises a plurality of pipes 6 to guide the liquid stream comprising urea from the distribution chamber to the collection chamber. The distribution chamber comprises a circular end adapted to fit with the decomposition section, a cylindrical wall 7 and a second end capped with a conical structure and comprising an inlet 5 for feeding the liquid stream comprising urea. A perforated cone 30, where its base diameter is about the same as the inlet, is located directly above the inlet, a second perforated plate 31 is located above the first cone 30. The second plate is a perforated hollow disk. The largest diameter of the second plate is 2 mm smaller than the diameter of the wall of the chamber. The third perforated plate 32 is located above the second plate and 10 mm below the inlets of the pipes 6. Its diameter is 2 mm smaller than the diameter of the wall of the chamber. The holes on the plate match with the inlets of the pipes 6. The three perforated plates are centered on and perpendicular to the main axis of the distribution chamber.

The invention claimed is:

1. A vertical distribution chamber for in an apparatus comprising a first chamber and a second chamber, wherein said apparatus is configured to operate with a bottom-to-top liquid flow, wherein the first chamber comprises a plurality of pipes for guiding a liquid stream from the distribution chamber to the second chamber and each pipe comprises a pipe opening fluidly connected to the distribution chamber, for evenly distributing a liquid stream to the plurality of pipe openings, the distribution chamber comprising:

a body comprising an open circular end, a capped circular end, and a cylindrical wall along a central axis joining the first open circular end and the second capped circular end, wherein:

the cylindrical wall has a same diameter as the open circular end and the capped circular end;

the open circular end is adapted to fit with the first chamber of the apparatus;

one inlet located on the capped circular end of the distribution chamber for feeding the liquid stream into the distribution chamber, wherein the inlet is centered on the central axis of the distribution chamber;

a series of stacked plates comprising at least a first perforated plate, a second perforated plate, and a third perforated plate, wherein:

the first perforated plate has a shape of a cone pointing towards the open circular end, is centered on and perpendicular to the central axis of the distribution chamber, is located directly above the inlet, a diameter of a base of the cone is 70% to 130% of a diameter of the inlet of the distribution chamber, and wherein the perforations make up from 1 to 10% of a surface of the first perforated plate;

the second perforated plate is a ring-shaped disk-like plate centered on the central axis of the distribution chamber, has an outer diameter of about the diameter of the cylindrical wall and an inner diameter of about the diameter of the base of the cone of the first perforated plate and wherein the perforations make up from 10 to 20% of the surface of the second perforated plate; and the third perforated plate is a disk with a diameter from 1 to 10 mm smaller than the diameter of the cylindrical wall, and is configured to be positioned from 5 mm to 25 mm directly below the inlets of the plurality of pipes, wherein each perforation in the third perforated plate is configured to align with a pipe opening in the first chamber and each pipe opening from the plurality of pipes of the first chamber has a corresponding perforation in the third perforated plate, each perforation is a circular through-hole and a diameter of each circular through-hole is 30% to 50% of a diameter of a pipe openings.

2. The distribution chamber according to claim 1, wherein the second perforated plate has a semi-toroidal shape.

3. The distribution chamber according to claim 2, wherein the second perforated plate comprises at least three sections: a first non-perforated truncated cone pointing towards the open circular end at a first angle, a second perforated truncated cone pointing towards the open circular end at a second angle and a third perforated truncated cone pointing towards the capped circular end, wherein a length of the wall of the first non-perforated truncated cone is from 1% to 10% of the diameter of the cylindrical wall; a top of the first truncated cone is joined to a base of the second truncated cone and a top of the second truncated cone is joined to a base of the third truncated cone.

4. The distribution chamber according to claim 3, wherein the wall of the first truncated cone which is not perforated forms an angle of 45° to 85°, with a base of the first truncated cone;

wherein the wall of the second truncated cone forms an angle of 10° to 30° with the base of the second truncated cone; and wherein the wall of the third truncated cone forms an angle of 30° to 60° with the base of the third truncated cone.

5. The distribution chamber according to claim 1, wherein the first perforated plate is a right circular cone with an angle between the cone axis and the cone surface comprised between 40° and 80°.

6. The distribution chamber according to claim 1, wherein the distribution chamber comprises a fourth perforated plate located between the second and the third perforated plates, wherein the fourth perforated plate is a disk that is centered on and perpendicular to the central axis of the distribution chamber, a diameter of the fourth perforated plate is 70% to 130% of the diameter of the inlet of the distribution chamber, and wherein the perforations make up from 3 to 10% of the surface of the fourth perforated plate.

7. The distribution chamber according to claim 3, wherein the diameter of a base of the first truncated cone of the second perforated plate is substantially the same as the diameter of the cylindrical wall.

8. The distribution chamber according to claim 3, wherein the diameter of a base of the first truncated cone of the second perforated plate is from 1 to 10 mm smaller than the diameter of the cylindrical wall.

9. The distribution chamber according to claim 1, wherein the diameter of the inlet of distribution chamber is from 0.35 to 3 m.

10. The distribution chamber according to claim 1, wherein the perforations of the third perforated plate are circular with a diameter of from 5 to 9 mm.

11. The distribution chamber according to claim 10, wherein the perforations of the third perforated plate are circular with a diameter of from 6 to 8 mm.

12. An apparatus comprising the first chamber, the second chamber, and the distribution chamber according to claim 1, wherein the first chamber comprises a plurality of pipes for guiding a liquid stream from the distribution chamber to the second chamber and each pipe comprises a pipe opening fluidly connected to the distribution chamber and to the second chamber.

13. The apparatus according to claim 12, wherein the third perforated plate is a disk which is positioned from 5 mm to 25 mm directly below the inlets of the plurality of pipes wherein each perforation in the third perforated plate is aligned with a pipe opening in the first chamber and each pipe opening from the plurality of pipes of the first chamber has a corresponding perforation in the third perforated plate.

14. The apparatus according to claim 13, wherein the third perforated plate is located from 7 mm to 15 mm directly below the inlets of the plurality of pipes.

15. The apparatus according to claim 13, wherein the third perforated plate is located about 10 mm directly below the inlets of the plurality of pipes.

16. The apparatus according to claim 12, wherein said apparatus is a vertical carbamate decomposer or a vertical urea concentrator.

17. A method to evenly distribute a liquid stream to a plurality of pipes to evenly distribute a liquid stream to a plurality of pipes, comprising a step of decomposing carbamate by feeding carbamate to the distribution chamber as defined in claim 1 wherein the apparatus is a carbamate decomposer or concentrating urea by feeding a urea solution to the distribution chamber wherein the apparatus is a urea concentrator.

18. A method to evenly distribute a liquid stream to a plurality of pipes, comprising a step of feeding the liquid stream into the distribution chamber as defined in claim 1, wherein a velocity of the liquid stream is from 0.2 to 2.0 m/s.

19. A method to decompose ammonium carbamate from a liquid stream comprising ammonium carbamate, comprising steps of:
 (i) feeding the liquid stream comprising ammonium carbamate to a carbamate decomposer comprising a heat exchanger comprising the plurality of pipes and the distribution chamber as defined in claim 1, wherein the plurality of pipes are straight, thereby evenly distributing the liquid stream comprising ammonium carbamate to the openings of the plurality of pipes, and
 (ii) heating up the plurality of pipes of the heat exchanger.

20. A method to concentrate an aqueous urea solution, comprising steps of:
 (i) feeding the aqueous solution to a concentrator comprising a heat exchanger comprising the plurality of pipes and the distribution chamber as defined in claim 1, wherein the plurality of pipes are straight, thereby evenly distributing the aqueous urea solution to the openings of the plurality of pipes, and
 (ii) heating up the plurality of pipes of the heat exchanger.

* * * * *